United States Patent [19]

Smith

[11] Patent Number: 4,482,647
[45] Date of Patent: Nov. 13, 1984

[54] MANUFACTURE OF OXYGENATED COMPOUNDS

[75] Inventor: David W. Smith, Cincinnati, Ohio

[73] Assignee: National Distillers and Chemical Corporation, New York, N.Y.

[21] Appl. No.: 573,538

[22] Filed: Jan. 25, 1984

Related U.S. Application Data

[63] Continuation of Ser. No. 326,978, Dec. 3, 1981, abandoned, which is a continuation of Ser. No. 142,284, Apr. 21, 1980, abandoned.

[51] Int. Cl.$^3$ .................... C07C 27/06; C07C 31/08
[52] U.S. Cl. .................................. 518/701; 518/126; 568/881
[58] Field of Search ................ 518/701, 726; 568/881

[56] References Cited

U.S. PATENT DOCUMENTS

| | | |
|---|---|---|
| 2,623,893 | 12/1952 | Kaufman . |
| 2,653,959 | 9/1953 | Moore et al. . |
| 2,672,476 | 3/1954 | Hujsak et al. . |
| 3,855,307 | 12/1974 | Rony et al. . |
| 3,944,588 | 3/1976 | Kaplan . |
| 3,948,965 | 4/1976 | Cawse . |
| 4,013,700 | 3/1977 | Cawse . |
| 4,096,164 | 6/1978 | Ellgen et al. . |
| 4,224,236 | 9/1980 | Wunder et al. . |
| 4,246,186 | 1/1981 | Bhasin et al. . |
| 4,288,558 | 9/1981 | Schmidt . |

Primary Examiner—Howard T. Mars
Attorney, Agent, or Firm—Kenneth D. Tremain

[57] ABSTRACT

Process of reacting carbon monoxide and hydrogen in the presence of halogen-containing rhodium catalysts to produce acetaldehyde and ethanol.

28 Claims, No Drawings

MANUFACTURE OF OXYGENATED COMPOUNDS

This is a continuation of co-pending application Ser. No. 326,978 filed Dec. 3, 1981, now abandoned which was a continuation of application Ser. No. 142,284, filed Apr. 21, 1980, now abandoned.

This invention is concerned with the production of acetaldehyde and ethanol by reaction of carbon monoxide and hydrogen in the presence of a rhodium catalyst.

Acetaldehyde is a very valuable commercial chemical with a wide variety of uses particularly as an intermediate for production of commercial chemicals. Ethyl alcohol is also an important valuable commercial chemical useful for a wide variety of purposes including as a chemical intermediate, as a solvent, and perhaps more importantly as a component of gasohol.

The reaction of carbon monoxide and hydrogen has long been known and can result in a variety of products depending on reaction conditions and the type of catalyst employed. U.S. Pat. No. 3,833,634 describes the reaction of carbon monoxide and hydrogen over rhodium catalyst to product ethylene glycol, propylene glycol, glycerol, methanol, ethanol, methyl acetate and other products. French Pat. No. 2,259,077 discloses producing ethanol from carbon monoxide and hydrogen using rhodium on silica gel as catalyst at 300°–350° C. and 1000–2500 psi pressure. West German specification No. 2,644,185 describes conversion of carbon monoxide and hydrogen to hydrocarbons employing $Ru_3(CO)_{12}$ in tetrahydrofuran as solvent. Use of the same ruthenium carbonyl catalyst on solid supports to produce hydrocarbon products is described in J.A.C.S. 100, 2590 (1978). The conversion of carbon monoxide and hydrogen over ruthenium carbonyl clusters to methanol and methyl formate has been described [ACS/CSJ Chemical Congress Abstracts, *INORG.* 428 (1979)].

THE INVENTION

It has now been found that the reaction of carbon monoxide and hydrogen over certain selected rhodium catalysts provides $C_2$-oxygenated products, that is acetaldehyde and ethanol. The reaction apparently proceeds in several stages, with acetaldehyde being the predominant product in the early stages and ethanol predominating in later stages, so that the process can give rise to one or the other product, or mixtures of these products, which can be readily separated as by fractionation. Thus, by controlling reaction parameters, the process can be controlled to produce one or the other product, as desired. Methanol is the principal by-product obtained in the present process.

If desired, the overall process of the invention can be conducted in separate stages, the initial stage resulting in production of acetaldehyde as the principal product, and the final stage resulting in production of ethanol as the principal product.

The very desirable results obtained in accordance with the present process renders the process particularly amenable to commercial production of acetaldehyde and ethanol, not only from the viewpoint of the substantial yields of the products, but also the ease of recovery from the co-produced methanol, e.g., by fractional distillation. The ease of recovery is extremely important since it permits separation of the products from the reaction mixture even in those process runs where methanol may be produced in substantial amount. Thus, for example, even where acetaldehyde is present in amounts corresponding to about 10 mole-percent, and even less, of the reaction product mixture, the ease of separation will permit recovery of the aldehyde.

Acetaldehyde is also produced in a high order of purity. Usually, the initial stage reaction mixture can be used as such in the final stage reaction to produce ethanol by reduction of acetaldehyde.

The results obtained with the present invention are indeed quite surprising and totally unexpected, particularly in view of the high conversions and specificity of the process in producing two-carbon oxygenated products.

DESCRIPTION OF THE PREFERRED EMBODIMENTS

The process of the present invention is accomplished by contacting carbon monoxide and hydrogen in the presence of certain rhodium-containing catalysts in a suitable solvent at elevated temperature and superatmospheric pressure. The major products of the reaction are acetaldehyde and ethanol, with the major by-product being methanol. The manner of contact is not critical since any of the various procedures normally employed in this type of reaction can be used as long as efficient gas-liquid contact is provided. Thus, the processes may be carried out by contacting the rhodium catalyst in reaction solvent with a mixture of carbon monoxide and hydrogen at the selected conditions. Where convenient, trickle phase operation can be used.

In view of the two-stage nature of the present process, the implementation can take several forms to produce ethanol. The reaction can be accomplished by allowing both stages to proceed consecutively at suitable temperature and pressure, or alternatively, the reaction can be stopped at the end of the first phase where the product is acetaldehyde and the second phase can be carried out under any applicable reduction process which will result in conversion of the aldehyde group of acetaldehyde to the primary alcohol group of ethanol.

A wide variety of reduction processes can be employed for the second phase reaction including the well-known chemical reducing agents employed in reducing aldehydes to primary alcohols. For commercial processes, however, where possible, catalytic reductions employing hydrogen are usually preferred since they are more practical and efficient especially with catalysts which can be regenerated and thus are re-usable. In the present process, catalytic hydrogenation is preferred for these same reasons, especially with catalysts which can be regenerated. Any hydrogenation catalyst can be employed.

Thus, typical hydrogenation catalysts include, for example, Raney Nickel, cobalt, copper chromite, rhodium, palladium, platinum, and similar such metal catalysts, which can be used conveniently on supports such as charcoal, silica, alumina, kieselguhr and the like. The conditions of catalytic hydrogenation are well-known and, in general, the reaction can be conducted at temperatures ranging from about 30° to about 150° C., usually at pressures of from about 100 to about 5000 psig. The use of higher temperatures and pressures, though operable, provides no special advantage and usually requires special equipment which economically is disadvantageous and therefore not preferred.

Particularly preferred hydrogenation catalysts are those which characteristically require short reaction times, e.g., palladium and nickel, which is most desirable for commercial processes for economic reasons.

The active catalyst species of the catalyst system for the present process has not been fully identified but it is assumed to be comprised of rhodium in complex combination with carbon monoxide together with a halide ligand. It is sufficient that the catalyst system initially comprise a source of rhodium and a source of halide and the active catalyst species then forms on initiation of the process, e.g., the complex rhodium carbonyl will form on addition of the reactants, i.e., carbon monoxide and hydrogen. Alternatively, the rhodium source can be a preformed complex carbonyl. Further, the source of both rhodium or rhodium carbonyl complex, and halide can be the same compound, e.g., rhodium carbonyl halides which are commercially available. The catalyst systems can be formed with rhodium carbonyl halides or alternatively by the combination of rhodium carbonyl or hydrocarbonyl complexes with a separate source of halide. The catalyst systems can be employed as such or deposited or affixed to a solid support such as molecular sieve zeolites, alumina, silica, ion exchange resin or a polymeric ligand. The preferred halides are chloride and bromide. The rhodium halocarbonyl catalysts may be represented by the formula $Rh_a(CO)_bX_c$ wherein a, b and c are integers and X is halide, preferably chloride. Such catalysts may be prepared by reaction of rhodium halides with carbon monoxide or by reaction of rhodium carbonyl complexes with halogen-containing compounds. Alternatively, rhodium carbonyl halides are available commercially, (e.g., from Matthey-Bishop, Malverne, PA).

The catalysts of this invention may contain other ligands in addition to halide ligand which must be present for the present process. As described in U.S. Pat. No. 3,833,634, suitable ligands are compounds which contain at least one nitrogen and/or at least one oxygen atom, said atoms having a pair of electrons available for formation of coordinate bonds with rhodium. Illustrative organic ligands include various piperazines, dipyridyls, N-substituted diamines, aminopyridines, glycolic acid, alkoxy-substituted acetic acids; tetrahydrofuran, dioxane, 1,2-dimethoxybenzene, alkyl ethers of alkylene glycols, alkanolamines, iminodiacetic acid, nitrilotriacetic acid, ethylenediaminetetraacetic acid and the like. In U.S. Pat. No. 3,527,809 are described phosphorus-containing ligands such as trialkyl, triaryl and tricycloalkyl phosphites and phosphines, as well as the analogous antimony and arsenic compounds.

The catalysts for this invention can be formed in situ by addition of halide to a suitable rhodium compound in the selected solvent or in the reaction mixture, if preferred. For example, rhodium acetylacetonate in combination with hydrogen halide in reaction solvents provides essentially the same results as preformed catalyst, e.g., $[Rh(CO)_2Cl]_2$. It is noted that, in the absence of hydrogen halide, e.g., HCl or HBr, the rhodium catalysts, such as rhodium carbonyl, form ethylene glycol, glycol aldehyde and methanol as the principal products with negligible or trace amounts of ethanol or acetaldehyde. The amounts of hydrogen halide added to the catalyst need not be stoichiometric since even small amounts will result in the production of some ethanol. For most purposes, however, it is preferred to employ at least an equimolar amount of hydrogen halide which can be added as aqueous hydrohalic acid or solution in organic solvents, such as the lower alkanols.

The determination of suitability of starting rhodium compounds to be used for in situ formation of the halide ligand-containing catalyst can be accomplished by a simple test procedure which involves running small scale reactions with the selected rhodium compound, hydrogen halide and reactants CO and $H_2$ in solvent. At the completion of the miniature reactions, gas-liquid chromatographic analyses of the reaction mixture will identify the products and, of course, will identify those rhodium compounds which are suitable, through in situ treatment, for production of ethanol and/or acetaldehyde. Using this test procedure, suitable starting rhodium compounds are easily identified.

Contrary to expectations, in the present process rhodium halocarbonyls appear to be poisoned by the presence of alkali metal compounds. For example, lithium chloride poisons $[Rh(CO)_2Cl]_2$, especially at high salt concentrations, for which reason alkali metal salts are to be avoided. This poisoning effect is particularly surprising in view of the known activating effect of alkali metal salts on the rhodium catalyzed conversion of CO and $H_2$ to ethylene glycol described in U.S. Pat. No. 3,833,634.

Catalysts formed in situ, however, appear to produce comparatively large quantities of methanol at times with lower acetaldehyde and ethanol. The preformed catalysts, however, only produce relatively low amounts of by-products and substantial yields of acetaldehyde and ethanol. In view of their higher selectivity for the $C_2$-oxygenated products of the invention, the preformed catalysts are preferred for production of acetaldehyde and ethanol.

The catalyst can be employed in soluble form or in suspension in the reaction medium, or alternatively deposited on porous supports.

When acetaldehyde is the desired product, of course, only the first stage reaction need be carried out. The product can be separated from the co-produced methanol, any ethanol formed and reaction solvent, if necessary, by fractional distillation.

The first stage reaction which results in acetaldehyde and methanol production is usually substantially complete in relatively short reaction times, usually less than about two hour, with only relatively minor amount, if any, of ethanol detected.

As should be apparent, the rhodium catalyst employed in the first stage reaction can also serve as the hydrogenation catalyst for the second stage reaction to produce ethanol. Thus, if the first phase reaction is allowed to continue, eventually the hydrogenation reaction will yield ethanol. In general, the rhodium catalyst of the first stage reaction is an effective catalyst for the second stage hydrogenation, but other hydrogenation catalysts can be used in lieu of the rhodium catalyst. If desired, the rhodium catalyst can be converted to a more effective hydrogenation catalyst by addition of a phosphine ligand, particularly triaryl phosphines such as triphenyl phosphine, although other phosphine ligands as described in U.S. Pat. No. 3,527,809 can be used as well.

It is possible to effect the reduction step over metal catalysts such as palladium and nickel, or copper chromite and to effect the second stage reaction in a separate reactor. Thus, the first stage reaction can be conducted in a first reactor under selected conditions of temperature and pressure, and after completion the first stage product, with or without isolation from the reaction mixture, can then be transferred to a second reactor under selected conditions of temperature and pressure to effect the hydrogenation reaction.

There of course is no criticality about stopping the reaction exactly at the termination of the first stage, or holding the second stage reaction until all acetaldehyde is reduced to ethanol. The reaction can be stopped at any convenient point which will be dictated by the product desired, along with other considerations. Thus, after substantially maximum yield of acetaldehyde is obtained, usually within about 2 hours the reaction can be stopped and the aldehyde recovered. However, the reaction mixture may contain quantities of ethanol formed through the second stage reaction. The products, however, are easily separable and are almost equally commercially important. Obviously, where ethanol is desired, the reaction can be allowed to proceed, within economic considerations, until reasonably complete to obtain ethanol as the major product, and of course acetaldehyde the minor product.

The present invention, therefore, provides a simplified process for selective production of acetaldehyde. In addition, this invention affords a simplified process for obtaining ethanol by either allowing the initial process for aldehyde production to continue so that hydrogenation yields ethanol or, alternatively, the aldehyde product of the first stage reaction is reduced employing art-recognized reduction processes to ethyl alcohol. In the latter process, the acetaldehyde product of the first stage reaction can be used in the form of the reaction mixture, or the product can be isolated, as by fractionation, and used in purified form.

The amount of catalyst employed in the present process does not seem to be critical and can vary considerably. At least a catalytically effective amount of catalyst should be used, of course. In general, an amount of catalyst which is effective to provide a reasonable reaction rate is sufficient. As little as 0.001 gram atoms of rhodium per liter of reaction medium can suffice while amounts in excess of 0.1 gram atoms do not appear to materially affect the rate of reaction. For most purposes, the effective preferred amount of rhodium is in the range of from about 0.002 to about 0.05 gram atoms per liter.

The reaction conditions are not overly critical in that wide ranges of elevated temperature and superatmospheric pressures are operable. The practical limitations of production equipment will dictate to a great extent the selection of temperatures and pressure at which the reaction is to be effected. Thus, using available production systems, the selected elevated temperature should be at least about 150° C. and can range up to about 300° C. For most purposes, the preferred operating temperature ranges from about 175° to about 275° C. The superatmospheric pressure should be at least about 10 atmospheres and can range up to almost any pressure attainable with production apparatus. Since extremely high pressure apparatus is quite expensive, pressures to about 700 atmospheres are suggested. Most desirably, the pressure should be in the range of from about 150 to about 400 atmospheres, particularly when employing the aforesaid preferred temperature range.

The reaction is preferably carried out in a solvent which will dissolve polar materials and which preferably is aprotic. The preferred solvents are N-substituted amides in which each hydrogen of the amido nitrogen is substituted by a hydrocarbon group, e.g., 1-methyl-pyrrolidin-2-one, N,N-dimethylacetamide, N,N-diethylacetamide, N-methylpiperidone, 1,5-dimethylpyrrolidin-2-one, 1-benzyl-pyrrolidin-2-one, N,N-dimethylpropionamide, hexamethylphosphoric triamide and similar such liquid amides. The amides are preferred solvents since their use results in the highest yields of product in present experience. Other solvents, usually aprotic, can be used but the yields are substantially less than obtained with the preferred amide solvents. Such solvents include, for example, cyclic ethers such as tetrahydrofuran, dioxane and tetrahydropyran; ethers such as diethyl ether, 1,2-dimethoxybenzene; alkyl ethers of alkylene glycols and polyalkylene glycols, e.g., methyl ethers of ethylene glycol, propylene glycol and di-, tri- and tetraethylene glycols; ketones such as acetone, methyl isobutyl ketone, and cyclohexanone; esters, such as ethyl acetate, ethyl propionate and methyl laurate; and alkanols, such as methanol, ethanol, propanol, 2-ethylhexanol and the like; tetramethylurea, $\gamma$-butyrolactone and mixtures thereof. The selected solvent should preferably be liquid under the reaction conditions.

The preferred solvents are aprotic organic amides. The contemplated amides include cyclic amides, i.e., in which the amido group is part of a ring structure such as in pyrrolidinones and piperidones; acylated cyclic amines, such as N-acyl piperidines, pyrroles, pyrrolidines, piperazines, morpholines, and the like, preferably in which the acyl group is derived from a lower alkanoic acid, e.g., acetic acid; as well as acyclic amides, i.e., wherein the amido group is not part of a ring structure as in acetamides, formamides, propionamides, caproamides and the like. The most preferred of the amides are those in which the amido hydrogen atoms are fully replaced by hydrocarbon groups preferably containing not more than 8 carbon atoms. Exemplary hydrocarbon groups are alkyl, preferably lower alkyl such as methyl, ethyl and butyl; aralkyl, such as benzyl and phenethyl; cycloalkyl, such as cyclopentyl and cyclohexyl; and alkenyl, such as allyl and pentenyl. The preferred amido nitrogen substituents are lower alkyl, especially methyl, ethyl and propyl groups and aralkyl groups, especially benzyl. The most preferred amide solvents include 1-methylpyrrolidin-2-one, 1-ethylpyrrolidin-2-one, and 1-benzylpyrrolidin-2-one. Of course, mixtures of the solvents can be used, e.g., amide solvent with other solvent.

Water is not critical to the reaction and can be present without serious adverse effect. It tends to react with carbon monoxide to form $CO_2$ and hydrogen (water gas shift). Water can be excluded since it can reduce the selectivity of conversion of carbon monoxide, or the water gas shift can be used advantageously to generate hydrogen.

The reaction pressures represent the total pressure of the gases contained ih the reactor, i.e., carbon monoxide and $H_2$, and, if present, any inert diluent gas such as nitrogen. As in any gaseous system, the total pressure is the sum of partial pressures of component gases. In the present reaction, the molar ratio of hydrogen to carbon monoxide can range from about 1/10 to about 10/1, with the preferred ratio, from about 1/5 to about 5/1, and the reaction pressure can be achieved by adjusting the pressure of these gases in the reactor.

Where the second phase reaction is carried out in a separate reactor whether over the originally present rhodium catalyst or a different metal hydrogenation catalyst, the reaction is normally conducted under hydrogen gas without diluent gas, as is usual in catalyzed hydrogenation reactions.

As with any process of this kind, the present process can be conducted in batch, semi-continuous, and continuous operation. The reactor should be constructed of materials which will withstand the temperatures and pressures required, and the internal surfaces of the reactor are substantially inert. The usual controls can be provided to permit control of the reaction such as heat-exchangers and the like. The reactor should be provided with adequate means for gas-liquid contact such as shaking, stirring, oscillation, trickle column operation and like methods. Catalyst as well as reactants may be introduced into the first stage or the second stage reactor at any time during the process for replenishment. Recovered catalyst, solvent and unreacted starting materials may be recycled.

The relative yields of ethyl alcohol, acetaldehyde and methanol are not overly critical since the product mixture can be readily separated into the components by known techniques, especially by fractional distillation, regardless of the proportions contained in the mixture. Therefore, even where the desired product is 10–20% of the reaction mixture, it can be readily separated from the mixture, especially under continuous processing. Of course, the preferred processes yield mixtures in which acetaldehyde and ethanol predominate as the reaction product and methanol, as a by-product, is minimal.

The process conditions for the separate first stage reaction are essentially the same as employed in the first stage of the combined two-stage reaction. Thus, the reaction is carried out at a temperature of at least about 150° C. to obtain a reasonable reaction rate. For best results, the temperature should be in the range of from about 175° C. to about 275° C., most preferably at about 200° C. The total pressure of gas used is generally maintained at from about 10 up to about 700 atmospheres, with from about 150 to about 600 atmospheres being preferred. Of course, higher pressures and higher temperatures can be used but with no appreciable advantage and, since they require the use of special high pressure equipment, they are usually avoided.

The reaction conditions employed in the second stage reaction, i.e., the hydrogenation, can be any of the standard reaction temperatures and pressures employed for such reactions since neither temperature nor pressure are critical for this reaction. Preferably, the hydrogenation is conducted at a temperature of at least about 100° C. in order to effect a reasonable reaction rate. Of course, lower temperatures can be used if longer reaction times can be tolerated. The pressure of hydrogen gas is not excessively critical as long as sufficient gas is available for the hydrogenation. For convenience, the pressure will range from about 500 psi to as much as 5000 psi, although even higher pressures can be employed.

When the catalyst selected for the hydrogenation step is other than rhodium, it is preferred to remove the rhodium catalyst from the first stage reaction mixture. This preference is primarily predicated on the desirability of avoiding concomitant catalytic effects which may tend to reduce the yield of ethanol.

The following examples further illustrate the invention. The equipment, synthetic procedure and analyses employed are as follows:

I. EQUIPMENT

A. Reactors

Reactions were carried out in Parr 71 ml reactors constructed of 310SS having one Type A ¼″ coned socket (Cat. #4740, Parr Instrument Co., Moline, IL). Glass liners with open tops were employed. Reactor seal was a modified Bridgeman type incorporating a special two piece gasket (Cat. #61HD), comprising silver (exposed to process) with a nickel back-up ring. This gasket arrangement was necessitated due to attack by carbon monoxide of the originally supplied one-piece nickel gasket.

The reactors were capped with 316SS Whitey severe service valves with high temperature Grafoil packing (Cat. #SS3NBS4-GTA-9K-3N, Whitey Co., Oakland, CA). The valves were coupled to the reactors with 316SS Sno-Trik male high pressure to Swagelok adapters (Cat. #SS-44M-A-400, Sno Trik Co., Solon, OH), and Swagelok port connectors (Cat. #SS-401-PC, Crawford Fitting Co., Cleveland, OH).

B. Agitation and Heating

The arm of a Burrell wrist action shaker was projected into an oven comprising an insulated box and electrical strip-heaters. Reactors were clamped to the shaker arm. Oven temperature was measured by a thermocouple which connected to a controller (on-off type). A timer was used to control reaction time by interrupting power to the temperature controller at the desired time. The temperature controller was used to activate a relay coil. A Variac was used to regulate the voltage going to the heater from the relay.

In cases where more vigorous agitation was required, the reactors (without glass liners) were bolted to a paint shaker by means of a special bracket which prevented whip action of the valve which would cause the port connector to sever.

C. Gas Compression and Delivery

Custom carbon monoxide-hydrogen mixtures (Union Carbide Corp., Linde Division, South Plainfield, NJ) were piped into an air driven, double-ended compressor (Cat. #46-14035, American Instrument Co., Silver Spring, MD), thence the reactor through a line containing shut-off and vent valves and a pressure gauge.

II. SYNTHESIS PROCEDURE

Reactor charging and sealing generally were carried out in a nitrogen atmosphere (glove bag). Catalyst (about 0.02 gm) and additives were weighed into a glass liner which then was placed in the reactor. Solvent (5 ml) and liquid additives (usually air free) were added by syringe or pipette. The reactor was sealed and capped with a valve.

The reactor was connected to the compressor discharge system and purged with the desired gas by pressurizing, then venting several times. Then gas was compressed into the reactor to the desired pressure (2000–4500 psig) as indicated on the system gauge. After gas feed-line venting, the reactor was disconnected, and the valve plugged to prevent leakage through the seal.

After heating (80°–250° C.) and shaking the reactor for the desired time, it was cooled then vented through a wet test meter with a gas sample being taken. The liquid contents were discharged, and the reactor and liner rinsed with solvent. The combined liquid for analysis was 15 gm.

III. GLC ANALYSIS PROCEDURE

GLC analyses were performed on a Varian-Aerograph Series 1400 Chromatograph equipped with hydrogen flame detector. A 6'×⅛" O.D. 316SS column packed with 80–100 mesh Chromosorb 101 was utilized. The column was operated at 100° C. for 9 minutes then temperature was increased by 6° C./min. to 200° C. This procedure provided reproducable isothermal analysis of lower boiling components and decreased retention times for higher boiling materials.

IV. PRODUCT IDENTIFICATION

The components of the reaction mixtures employing Rh catalysts were identified by GLC-MS analysis.

EXAMPLE 1

Using the described Synthesis Procedure, a mixture of 1.5:1 $H_2$/CO at 4500 psig (20° C.) was charged into the reactor with 5 ml N-methylpyrrolidin-2-one and the rhodium halocarbonyl and the mixture heated for two hours. The results are given in TABLE 1 which includes the poisoning effect of lithium chloride.

TABLE 1

| Catalyst | mMole Metal | Additive, mMole | | Temp., °C. | Product Yields, mMoles | | | Turnover Number Moles Product/Mole Metal | |
|---|---|---|---|---|---|---|---|---|---|
| | | | | | $CH_3OH$ | $CH_3CHO$ | $C_2H_5OH$ | $C_1$ | $C_2$ |
| [Rh(CO)$_2$Cl]$_2$ | .129 | — | — | 175 | .066 | .012 | 046 | .5 | .4 |
| [Rh(CO)$_2$Cl]$_2$ | .129 | LiCl | .129 | 200 | .023 | .013 | 0 | .2 | .1 |
| [Rh(CO)$_2$Cl]$_2$ | .129 | — | — | 200 | .24 | tr. | .056 | 1.9 | .4 |
| [Rh(CO)$_2$Cl]$_2$ | .129 | LiCl | .75 | 200 | 0 | 0 | 0 | 0 | 0 |
| [Rh(CO)$_2$Cl]$_2$ | .098 | LiCl | .75 | 200 | 0 | 0 | 0 | 0 | 0 |

What is claimed is:

1. A process for forming acetaldehyde in a first stage reaction and then reducing said aldehyde to form ethanol in a second stage reaction which comprises reacting carbon monoxide and hydrogen at a temperature of from about 150° to about 300° C. and at superatmospheric pressure in the presence of a liquid catalyst system consisting of a rhodium carbonyl halide or a combination of a rhodium carbonyl complex and a separate source of halide selected from the group consisting of hydrogen halides in a solvent in which said catalyst components are dissolved at least during said first reaction stage, then catalytically reducing said formed acetaldehyde and recovering ethanol as the principal product.

2. A process according to claim 1 wherein said rhodium is present during said second reaction stage.

3. A process according to claim 1 wherein a hydrogenation catalyst is present during said second stage reaction.

4. A process according to claim 3 wherein said rhodium is removed from the first reaction stage product prior to said second stage reaction.

5. A process according to claim 3 wherein said hydrogenation catalyst comprises palladium.

6. A process according to claim 1 wherein said first and second stage reactions are conducted at a temperature of from about 175° to about 275° C.

7. A process for producing acetaldehyde which comprises reacting carbon monoxide and hydrogen at a temperature of from about 150° to about 300° C. and at superatmospheric pressure in the presence of a liquid catalyst system consisting of a rhodium carbonyl halide or a combination of a rhodium carbonyl complex and a separate source of halide selected from the group consisting of hydrogen halides in a solvent in which said catalyst components are dissolved and recovering acetaldehyde as the principal product from said reaction.

8. A process according to claim 7 wherein said temperature is in the range of from about 175° to about 275° C. and said pressure is in the range of from about 150 to about 600 atmospheres.

9. A process according to claim 7 wherein the molar ratio of hydrogen to carbon monoxide is from about 1/10 to about 10/1.

10. A process according to claim 7 wherein said solvent is an aprotic organic amide.

11. A process according to claim 10 wherein the solvent comprises an N-lower alkyl pyrrolidin-2-one.

12. A process according to claim 10 wherein the solvent comprises an N,N-di(lower alkyl) acetamide.

13. A process according to claim 10 wherein the solvent comprises N-methyl pyrrolidin-2-one.

14. A process according to claim 10 wherein the solvent comprises N,N-diethyl acetamide.

15. A process according to claim 10 wherein the solvent comprises N,N-diethyl propionamide.

16. A process for producing a mixture of ethanal and acetaldehyde which comprises forming acetaldehyde in a first stage reaction by reacting carbon monoxide and hydrogen at a temperature of from about 150° to about 300° C. and at superatmospheric pressure in the presence of a liquid catalyst system consisting of a rhodium carbonyl halide or a combination of a rhodium carbonyl complex and a separate source of halide selected from the group consisting of hydrogen halides in a solvent in which said catalyst components are dissolved to form acetaldehyde and, optionally, a minor amount of ethanol, and then catalytically reducing a portion of said acetaldehyde to form ethanol in a second stage reaction and thereby form a mixture of ethanol and acetaldehyde, and recovering said ethanol and acetaldehyde.

17. A process according to claim 1 wherein the solvent comprises an N-lower alkyl pyrrolidin-2-one.

18. A process according to claim 1 wherein the solvent comprises N-methyl pyrrolidin-2-one.

19. A process according to claim 16 in which said first stage reaction is conducted at a temperature of from about 175° to about 275° C. and at a pressure of from about 150 to about 400 atmospheres.

20. A process as in claim 16 in which said rhodium component is present during said second reaction stage.

21. A process as in claim 16 in which a hydrogenation catalyst is present during said second stage reaction.

22. A process as in claim 18 in which said rhodium component is removed from the first reaction stage product prior to said second stage reaction.

23. A process as in claim 18 in which said hydrogenation catalyst comprises palladium.

24. A process as in claim 16 wherein said rhodium carbonyl halide complex is preformed.

25. A process as in claim 16 wherein said solvent is an aprotic organic amide.

26. A process according to claim 25 wherein the solvent comprises an N,N-di(lower alkyl) acetamide.

27. A process according to claim 25 wherein the solvent comprises N,N-diethyl acetamide.

28. A process according to claim 25 wherein the solvent comprises N,N-diethyl propionamide.

* * * * *